(12) United States Patent
Kim et al.

(10) Patent No.: US 8,192,751 B2
(45) Date of Patent: Jun. 5, 2012

(54) COMPOSITION FOR PROMOTING BONE REGENERATION AND RESTORATION

(75) Inventors: Jin-Young Kim, Cheonan (KR); Jae-Hyoung Ahn, Daejeon (KR); Seok-Beam Song, Daejeon (KR); Ji-Hwa Chae, Daejeon (KR); Seog-Jin Seo, Daejeon (KR); Ke-Won Kang, Daejeon (KR); Ho-Chan Hwang, Seoul (KR); Jung-Suk Lee, Daejeon (KR)

(73) Assignee: Hans Biomed.Cor (KR)

( * ) Notice: Subject to any disclaimer, the term of this patent is extended or adjusted under 35 U.S.C. 154(b) by 189 days.

(21) Appl. No.: 12/523,264

(22) PCT Filed: Oct. 17, 2007

(86) PCT No.: PCT/KR2007/005090
§ 371 (c)(1),
(2), (4) Date: Jan. 14, 2010

(87) PCT Pub. No.: WO2008/088117
PCT Pub. Date: Jul. 24, 2008

(65) Prior Publication Data
US 2010/0129421 A1    May 27, 2010

(30) Foreign Application Priority Data
Jan. 15, 2007    (KR) .................. 10-2007-0004362

(51) Int. Cl.
*A61F 2/00* (2006.01)
*A61K 9/14* (2006.01)
*A61K 47/38* (2006.01)

(52) U.S. Cl. ........ 424/423; 424/426; 424/484; 514/781; 514/944

(58) Field of Classification Search .................. None
See application file for complete search history.

(56) References Cited

U.S. PATENT DOCUMENTS

| | | | |
|---|---|---|---|
| 5,510,396 A | 4/1996 | Prewett et al. | |
| 2002/0098222 A1* | 7/2002 | Wironen et al. | 424/423 |
| 2002/0160032 A1 | 10/2002 | Long et al. | |
| 2003/0009235 A1 | 1/2003 | Manrique et al. | |

FOREIGN PATENT DOCUMENTS

| | | |
|---|---|---|
| WO | 9938543 | 8/1999 |
| WO | 0074690 | 12/2000 |
| WO | 2004011053 | 2/2004 |
| WO | 2005/072656 A1 | 8/2005 |

OTHER PUBLICATIONS

Extended European Search Report for application No. 07833399.4-1219/2114457 dated Jan. 15, 2010.
Chinese Office Action—Chinese Application No. 200780049891.8 issued on Nov. 3, 2010, citing US5,510,396 which was previously submitted.
International Search Report for PCT Application No. PCT/KR2007/005090 dated Jan. 4, 2008.
Written Opinion for PCT Application No. PCT/KR2007/005092 dated Jan. 4, 2008.
Daniel A. Oakes et al., "An Evaluation of Human Demineralized Bone Matrices in a Rat Femoral Defect Model", Clinical Orthopaedics and Related Research, Aug. 2003, No. 413, pp. 281-290.
John E. Feighan et al., "Induction of Bone by a Demineralized Bone Matrix Gel: A Study in a Rat Femoral Defect Model", Journal of Orthopaedic Research, Nov. 1995, vol. 13 No. 6, pp. 881-891.
LuAnne McKinney et al., "A Bone Regeneration Study: Transforming Growth Factor-β1 and Its Delivery" Journal of Craniofacial Surgery, vol. 7., No. 1, Jan. 1996, pp. 36-45.

* cited by examiner

*Primary Examiner* — Ernst Arnold
(74) *Attorney, Agent, or Firm* — Cantor Colburn LLP

(57) ABSTRACT

A bone grafting material composite is provided. The bone grafting material composite includes a demineralized bone matrix (DBM) and a carboxymethyl cellulose (CMC)/glycerol gel carrier. Due to the CMC/glycerol gel carrier, the implantation ability thereof is better than that of the DBM. Therefore, the bone grafting material composite can be easily used, so that a curative effect can be greatly improved. In addition, since the CMC/glycerol gel is used as a carrier, the composite with a mobility maintained is washed out by water after surgery, so that the composite can be fixed on a damaged portion of a bone.

3 Claims, 2 Drawing Sheets

[Figure 1]
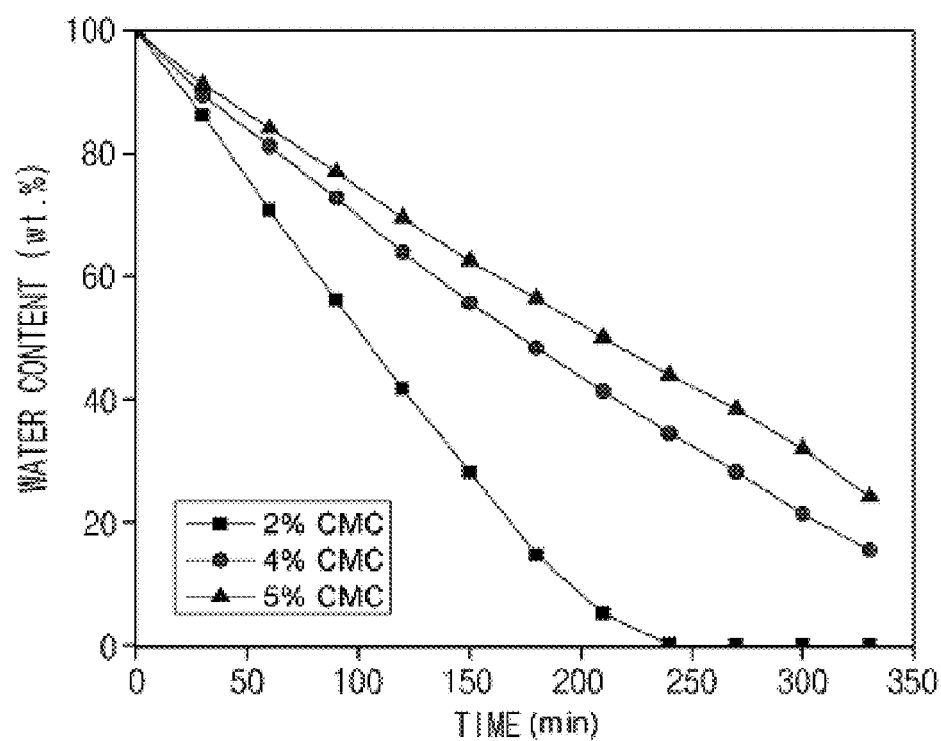

[Figure 2]
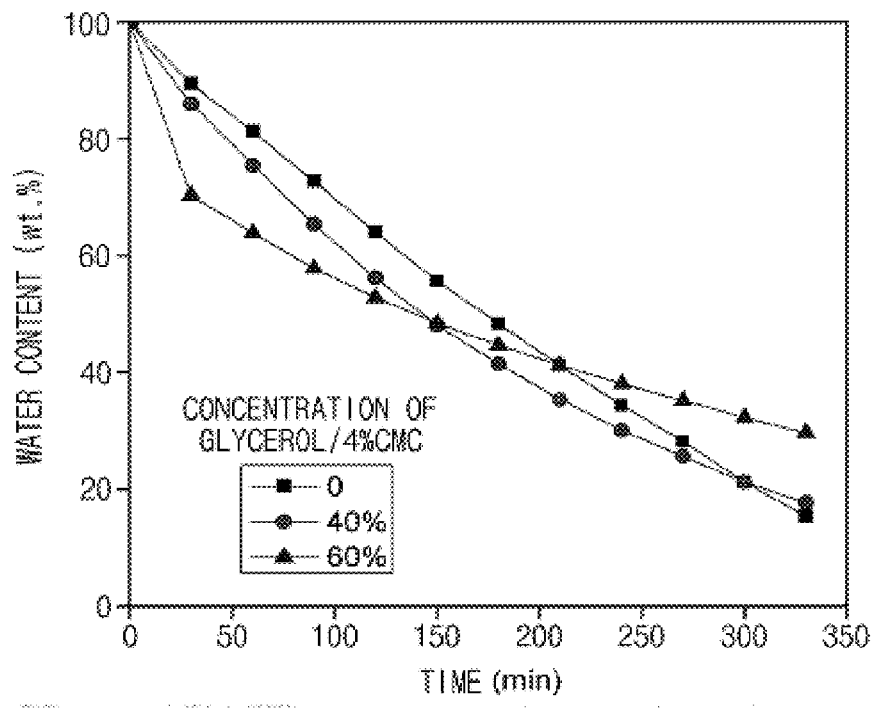
[Figure 3]
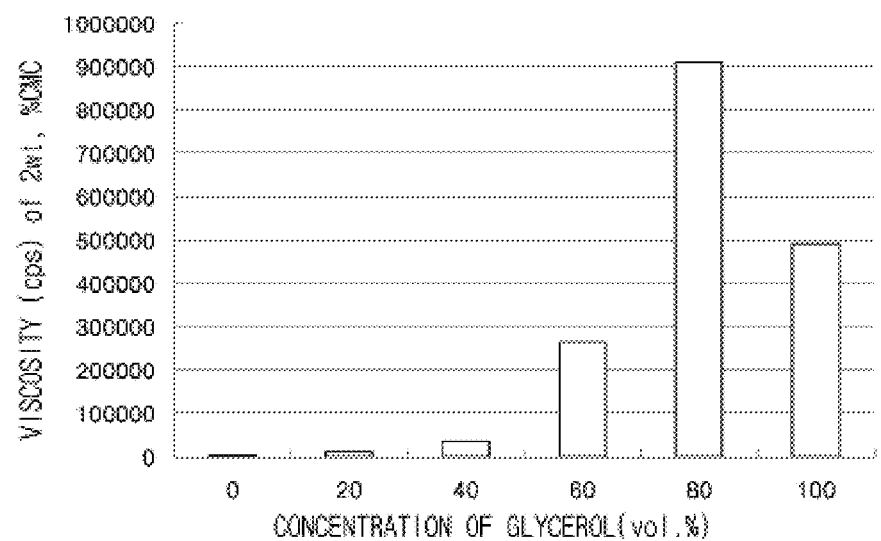

COMPOSITION FOR PROMOTING BONE REGENERATION AND RESTORATION

TECHNICAL FIELD

The present invention relates to a composite of a demineralized bone matrix (DBM) capable of being used for an effective bone grafting material, having a good compatibility to a body fluid, and stabilizing a high-content DBM for grafting a bone to a human body.

BACKGROUND ART

A bone is made of organic materials and inorganic materials. The organic materials include growth factors, soft bone tissues, collagen, other proteins, and the inorganic materials include calcium phosphate.

A bone grafting material needs to have a biocompatibility so as to facilitate natural regeneration in case of occurrence of defects or wounds of the bone. An ideal bone grafting material needs to have a bone generation function, that is, a bone conduction function and a bone induction function and to be easy to operate for surgery. In addition, strength and properties thereof needs to be maintained after the surgery.

A demineralized bone matrix (DBM) improves activity of bone generation protein included in the bone to increase the bone induction function and is easy to treat. Therefore, the DBM has been increasingly used for the bone grafting surgery, and the DBM is considered as an effective bone grafting material for treatment. In order to graft the DBM into a wound portion, a method of delaying absorption of the DBM, increasing the activity for combining with the bone, and being easily treated is required.

The DBM denotes a polymer material obtained by removing cells and inorganic materials from a bone. Since the DBM is a material for inducing hard tissue generation, various applications thereof are expected.

Since the DBM has an efficient bone regeneration capability, the DBM is used as a filler for a portion of a body where bone regeneration is slow or impossible in orthopedics, dentistry, neurosurgery, and the like. In addition, the DBM is used to replace a damaged portion of a bone and to fix and reinforce a joint. In addition, the DBM is used to treat an osteoma, a bone wound, and a bone fracture.

Since the DBM has a low compatibility to an aqueous solution due to a structure thereof, the DBM cannot easily maintain a desired shape when only the DBM is used for grafting. In addition, a bone generation protein included in the DBM may be digested in a body. Therefore, the DBM is not easy to maintain a shape and has a slow bone regeneration rate, so that the DBM becomes an incomplete replacement. In addition, since the DBM has no implantation ability, other materials are necessarily used for grafting of the DBM into a damaged portion of a bone.

According to current reports, since the DBM has low implantation ability due to the incomplete shape retentivity of the DBM, a composite of the DBM and polymers such as gelatin, glycerol, poloxamer, and hyaluronic acid has been used. However, the aforementioned stabilizers do not satisfy all the requirements of the shape retentivity, the implantation ability, the content, and the biocompatibility. For example, a composite including gelatin can improve the implantation ability of the DBM, but the composite is not easy to store and has a short expiration period A method of grafting a mixture of the DBM and a synthetic polymer is also disclosed. However, since the mixture is not digested in a body, a compatibility to a body fluid is lowered, so that the mixture may damage kidney. In addition, a mixture of the DBM and glycerol is also disclosed. However, since the mixture has a very small content of the DBM, the bone regeneration function of the DBM may be lowered. In addition, a mixture of the DBM and hyaluronic acid is also disclosed. However, the grafting of a bone into is too rapidly digested in a body and production cost thereof is two high. In addition, due to the hyaluronic acid, a bone morphogenic protein (BMP) is easily exposed, so that the BMP is rapidly digested by an enzyme in a body. Therefore, the bone regeneration rate is lowered.

In order to solve the problems, there is a need for a composite capable of improving a biocompatibility, having no damage to a human body, improving an implantation ability and shape retentivity of a DBM, and having no fluidness after grafting.

DISCLOSURE

Technical Problem

The present invention provides a composite of demineralized bone matrix (DBM)-carboxymethyl cellulose (CMC)/glycerol using a cellulose-based CMC and glycerol as an DBM stabilizer so as to obtain a good compatibility to a body fluid and to stabilize a high-content DBM for grafting a bone to a human body.

Technical Solution

A stability of a bone grafting material is important in that the bone grafting material may be an infection channel for an acquired immuno deficiency syndrome or lethal infection. Therefore, a bone grafting material product of which immunologic rejection and stability are tested is required.

The bone grafting material uses bone inductivity and bone conductivity. Since a lyophilized bone contains minerals, the bone grafting material serves as a scaffold to form a bone through bone conduction. In a case where bone grafting is performed on maxillary sinus by using the lyophilized bone, after sixth months, a cartilage material is observed, and a hard tissue similar to a bone is formed. The lyophilized bone is used based on the fact that a BMP of a bone matrix is exposed through a demineralization process and a bone is formed through bone induction.

As a material for a bone grafting material, a DBM is used. The DBM is a bone powder having only protein excluding inorganic material among bone ingredients. A mixture of the DBM and an aggregating material is used as the bone grafting material. In this case, the bone may be obtained from an animal bone or a human bone.

A biocompatible aggregating material is a water-soluble material. Just after the bone grafting material is grafted in a body, the aggregating material is dissolved out from the bone grafting material, so that the bone grafting material has a large porosity. The large porosity increases an accessibility of the bone grafting material, so that activities of osteocyte and osteoblast in a grafted portion can be increased. Accordingly, the bone conductivity of the bone grafting material can be increased.

Among carriers, a poloxamer cannot be digested in a body and has a low compatibility to a body fluid, so that it may damage kidney. A mixture of the DBM and glycerol has a low DBM content.

In addition, a mixture of the DBM and hyaluronic acid is rapidly digested in a body. Therefore the BMP is exposed to be digested by an enzyme in a body. Accordingly, the bone regeneration rate may be lowered.

A sodium CMC carboxymethyl cellulose is an aqueous cellulose that is used as an viscous, non-toxic, hygroscopic, odorless food additive. Since the CMC has a good compatibility to a body fluid, the CMC is oozed into the body fluid so as to stabilize the DBM. A DBM bone grafting material, that is, a mixture of the DBM and the CMC carrier according to the present invention has a concentration of a gel, the DBM bone grafting material is not dissolved into water, but it is maintained at the grafted portion.

The present invention provides a composite matrix composite including the DBM and the CMC/glycerol gel carrier.

The present invention provides a composite matrix composite, that is, a mixture of the DBM for inducing bone formation and the CMC and glycerol, a non-toxic stabilizer for transferring the DBM and stabilizing the DBM.

According to the present invention, a CMC/glycerol gel is used as a carrier, the implantation ability of the composite matrix composite is better than that of the DBM, so that the composite matrix composite can be easily used. As a result, a curative effect can be greatly improved. That is, the CMC and glycerol as the stabilizer for the composite matrix composite prevents the bone induction factor included in the DBM from being digested by a proteinase. In addition, the CMC and glycerol can transfer the DBM and be safely and conveniently used for a grafted portion.

A time duration of water content of a CMC gel is increased as the concentration thereof is increased from a low-concentration to a high-concentration. Particularly, since low-concentration (2%) CMC gel is flown, properties thereof is deteriorated. A high-concentration (8%) CMC gel has a large water content, but it is difficult to handle. Therefore, preferably, the concentration of the CMC in the CMC/glycerol gel carrier aqueous solution is in a range of 3 to 8%.

In addition, preferably, the concentration of the glycerol in the CMC/glycerol gel carrier aqueous solution is in a range of 20 to 90%. Preferably, a concentration of the DBM is in a range of 30 to 90% with respect to a total of bone regeneration promoting composite The bone regeneration promoting composite may further include a cancellous bone piece, a compact bone piece, hydroxy apatite, and tricalcium phosphate.

In order to improve a bone conductivity, a composite of DBM-CMC/glycerol-cancellous bone may be produced by adding a cancellous bone piece, a compact bone piece, a hydroxy apatite, and a tricalcium phosphate to a composite of the DBM and CMC/glycerol gel carrier. Preferably, the concentration of the DBM is in a range of 10 to 90% with respect to a total composite.

Advantageous Effects

According to the present invention, a CMC/glycerol gel is used as a carrier, the implantation ability of the composite matrix composite is better than that of the DBM, so that the composite matrix composite can be easily used. As a result, a curative effect can be greatly improved.

In addition, since the CMC/glycerol gel is used as a carrier, the composite with a mobility maintained is washed out by water after surgery, so that the composite can be fixed on a damaged portion of a bone. In order to improve a bone conductivity, a composite of DBM-CMC/glycerol-cancellous bone can be produced by adding a cancellous bone piece to a composite of the DBM and CMC/glycerol gel carrier.

According to the present invention, the DBM composite can be used in a syringe type for grafting the DBM composite into a bone deficient portion or in a putty type for applying the DBM composite on the bone deficient portion with a hand. In addition, since the implantation ability of the DBM composite is improved, a shape thereof can be retained for a long time, and functions of the DBM can be improved.

While the present invention has been particularly shown and described with reference to exemplary embodiments thereof, it will be understood by those of ordinary skill in the art that various changes in form and details may be made therein without departing from the spirit and scope of the present invention as defined by the following claims.

DESCRIPTION OF DRAWINGS

FIG. 1 is graph illustrating a change in water content according to time, measured with respect to concentrations of CMC.

FIG. 2 is a graph illustrating a change in water content according to time, measured with respect to concentrations of glycerol.

FIG. 3 is a graph illustrating a viscosity of CMC according to a concentration of glycerol.

BEST MODE

Referring to a change in water content with respect to concentrations of carboxymethyl cellulose (CMC) shown in FIG. 1, a time duration of the water content is increased as the concentration of the CMC gel is increased from a low-concentration to high-concentration. Particularly, since low-concentration (2%) CMC gel is flown, properties thereof is deteriorated. A high-concentration (8%) CMC gel has a large water content, but it is difficult to handle. Therefore, preferably, the concentration of the CMC in the CMC/glycerol gel carrier aqueous solution is in a range of 3 to 8%.

In addition, preferably, the concentration of the glycerol in the CMC/glycerol gel carrier aqueous solution is in a range of 20 to 90%.

Different concentrations of glycerol are added to 4% CMC gel, and time duration of the water content thereof is tested. As shown in FIG. 2, it can be understood that a change in water content of a composite gel in a 4% CMC gel-based is increased as the concentration of glycerol is increased.

In a case where the concentration of glycerol is 60%, since the time duration of water content of 60%-glycerol composite gel is longer than that of the low-concentration glycerol composite gel at the time of 150 min, the time duration of the water content of 60%-glycerol composite gel is larger than that of a single CMC gel. Therefore, it can be understood that the performance of the new composite gel is increased and the time duration of water content of the DBM gel is longer than that of the single CMC gel, so that it is possible to extend an expiration period.

FIG. 3 is a graph illustrating a viscosity of CMC according to a concentration of glycerol. As seen in Table 1, as the concentration of glycerol is increased, the viscosity of CMC is increased.

TABLE 1

| Concentration of glycerol (vol. %) | Viscosity of 2% CMC (cps) |
| --- | --- |
| 0 | 2360 |
| 20 | 10546 |
| 40 | 36913 |
| 60 | 265000 |
| 80 | 910000 |
| 100 | 491000 |

Preferably, a concentration of the DBM is in a range of 30 to 90% with respect to a total of bone regeneration promoting composite.

In order to improve a bone conductivity, a composite of DBM-CMC/glycerol-cancellous bone may be produced by adding a cancellous bone piece, a compact bone piece, a hydroxy apatite, and a tricalcium phosphate to a composite of the DBM and CMC/glycerol gel carrier. Preferably, the concentration of the DBM is in a range of 10 to 90% with respect to a total composite.

The bone regeneration promoting composite according to the present invention may further include a bone density promoting drug, a growth factor, glucosamine, and calcium phosphate including cytokine.

Hereinafter, a bone grafting material production process will be described more in detail.

1. Bone Grafting Material Manufacturing Process

A soft tissue is removed from a bone which is stored in cyrorefrigerator in an aseptic state. The bone with the soft tissue removed is immersed into ether to remove fat therefrom. The defatted bone is dried, and the dried bone is cut and inserted into a powdering machine. The powdered bone powder is sieved according to a size thereof and, then, demineralized in a hydrochloric acid solution. The resulting product is sterilized by using ethylene oxide and inserted into a lyophilizer.

2. Mixing and Grafting (1) Gel

The powdered DBM and a low-concentration (4%) CMC sodium salt solution are taken with predetermined quantities and mixed in a mixer for a sufficient time. Next, a gel is taken out by using a 10 cc syringe. The syringe filled with the gel is separated. By pushing a plunger, bubbles and empty spaces of the syringe are removed.

A break-off tip is connected to an outlet of the syringe. The completed product is inserted into an inner pouch and sealed with a package apparatus. The gel-type DBM composite is grafted into a bone deficient portion.

(2) Putty

The powdered DBM and a high-concentration (5%) CMC sodium salt solution are taken with predetermined quantities and mixed in a mixer for a sufficient time. Next, a predetermined amount of a putty is produced by using a spatula and a spoon.

The putty-type DBM composite is applied on a bone deficient portion with a hand.

A clinical trial test of the bone regeneration promoting composite according to the present invention was practiced.

The bone grafting material according to the present invention was grafted for a patient having pain and flail of lower right second molar tooth under the condition that the tooth may be pulled out. After one year from the grafting, the patient has no pain and no flail. A bone tissue on the grafted portion was sampled, HE tissue examination and MT staining were performed. The bone generation can be recognized through comparison of X-ray photographs before and after the bone grafting.

The invention claimed is:

1. A bone regeneration promoting composite comprising:
    a demineralized bone matrix (DBM); and
    a carboxymethyl cellulose (CMC)/glycerol gel carrier;
    wherein
    a concentration of the CMC is in a range of 3 to 8% with respect to a CMC/glycerol gel carrier aqueous solution;
    a concentration of the glycerol is in a range of 20 to 90% with respect to the CMC/glycerol gel carrier aqueous solution;
    a concentration of the DBM is in a range of 30 to 90% with respect to a total bone regeneration promoting composite.

2. The bone regeneration promoting composite according to claim 1, further comprising a cancellous bone piece, a compact bone piece, a hydroxy apatite, and a tricalcium phosphate.

3. The bone regeneration promoting composite according to claim 1, further comprising a bone density promoting drug, a growth factor, glucosamine, a calcium phosphate and a cytokine.

* * * * *